United States Patent [19]

Bajusz et al.

[11] Patent Number: 4,804,405
[45] Date of Patent: Feb. 14, 1989

[54] ELECTIVE HERBICIDE COMPOSITIONS HAVING A PROLONGED ACTION CONTAINING α-CHLOROACETAMIDE DERIVATIVES AS ACTIVE INGREDIENT

[75] Inventors: Ferenc Bajusz; Károly Balogh; Tibor Bódi, all of Miskolc; Barna Bordás, Budapest; Zsolt Dombay, Miskolc; Gyöngyvér Fodor née Balogh, Miskolc; Erzsébet Grega née Tóth, Miskolc; Pál Gribovszki, Miskolc; Ernő Lőrik, Miskolc; György Matolcsy, Budapest; Judit Mátyás née Dávid, Sajóbábony; Erzsébet Mile, Miskolc; József Nagy, Miskolc; Csaba Pavliscsák, Sajóbábony; Gyula Tarpai, Miskolc; András Tóth, Miskolc; István Tóth, Miskolc; Mária Tóth née Takács, Miskolc; Márton Tüske, Budapest, all of Hungary

[73] Assignee: Eszakmagyarországi Vegyimüvek, Sajóbábony, Hungary

[21] Appl. No.: 787,912

[22] Filed: Oct. 16, 1985

[30] Foreign Application Priority Data

Oct. 16, 1984 [HU] Hungary .............................. 3856/84

[51] Int. Cl.⁴ .............................................. A01N 25/22
[52] U.S. Cl. .......................................... 71/118; 71/121
[58] Field of Search ................................. 71/118, 121

[56] References Cited

U.S. PATENT DOCUMENTS

| | | | |
|---|---|---|---|
| 2,791,606 | 5/1957 | Dorman et al. | 71/100 X |
| 2,863,752 | 12/1958 | Hamm | 71/118 |
| 2,864,683 | 12/1958 | Hamm | 71/118 |
| 3,442,945 | 5/1969 | Olin | 71/118 X |
| 3,893,838 | 7/1975 | Pallos | 71/100 |
| 3,931,313 | 1/1976 | Baker | 260/561 H |
| 4,695,313 | 9/1987 | Bordas et al. | 71/100 |
| 4,702,762 | 10/1987 | Camaggi et al. | 71/90 |
| 4,740,236 | 4/1988 | Topfi | 71/103 |

OTHER PUBLICATIONS

Felix et al., Chem. Abst. vol. 99(1983) 100959g.
Rehn et al. Chem. Abst. vol. 89 (1978) H8929z.

Primary Examiner—Catherine L. Mills
Attorney, Agent, or Firm—Schweitzer & Cornman

[57] ABSTRACT

The invention relates to compositions useful for prolonging the action and increasing the selectivity of herbicide compositions containing α-chloroacetamide derivatives as active ingredient as well as to highly selective herbicide compositions containing α-chloroacetamide derivatives as active ingredients and optionally an antidote wherein an animal derivative of the general formula (III) is used for achieving the prolonged action and increased selectivity. In the formula (III)

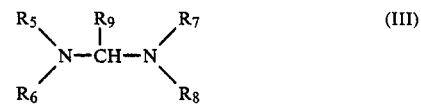

$R_5$, $R_6$, $R_7$ and $R_8$ stand independently for hydrogen, a $C_{1-6}$ alkyl, $C_{3-7}$ cycloalkyl or $C_{2-5}$ alkenyl group optionally substituted by a $C_{1-4}$ alkyl group; and
$R_9$ stands for hydrogen or a $C_{1-4}$ alkyl group optionally substituted by halogen, or a phenyl group.

10 Claims, No Drawings

ELECTIVE HERBICIDE COMPOSITIONS HAVING A PROLONGED ACTION CONTAINING α-CHLOROACETAMIDE DERIVATIVES AS ACTIVE INGREDIENT

The invention relates to compositions useful for prolonging the action and increasing the selectivity of herbicide compositions containing α-chloroacetamide derivatives as active ingredient as well as to highly selective herbicide compositions containing α-chloroacetamide derivatives as active ingredients and optionally an antidote wherein an aminal derivative of the general formula (III) is used for achieving the prolonged action and increased selectivity. In formula (III)

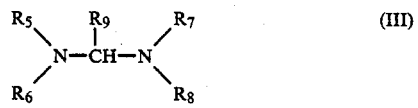

$R_5$, $R_6$, $R_7$ and $R_8$ stand independently for hydrogen, a $C_{1-6}$ alkyl, $C_{3-7}$ cycloalkyl or $C_{2-5}$ alkenyl group optionally substituted by a $C_{1-4}$ alkyl group; and $R_9$ stands for hydrogen or a $C_{1-4}$ alkyl group optionally substituted by halogen, or a phenyl group.

The above-mentioned alkyl or alkenyl substituents may contain a straight or branched chain. The alkyl group may be e.g. a methyl, ethyl, propyl, isopropyl, butyl, isobutyl or a tertiary butyl group. An advantageous alkenyl group is the allyl (i.e. 2-propenyl) group. A preferred cycloalkyl group is the cyclohexyl group.

$R_9$ as halogen is preferably chlorine. The alkyl group may be substituted by one or more halogens. $R_9$ is preferably hydrogen or a methyl, ethyl or trichloromethyl group.

The preferred aminal derivatives of formula (III) are the compounds containing at least two allyl groups, particularly N,N'-diallyl substituted compounds. The N,N'-dialkyl-N,N'-diallyldiaminomethane derivatives and N,N,N',N'-tetraallyl derivatives such as N,N,N',N'-tetraallyldiaminomethane are particularly advantageous.

α-Chloroacetamide derivatives as active ingredients of efficient herbicides are wide-spread in the agricultural practice. α-Chloroacetamide and herbicide compositions containing them are reported e.g. in the U.S. Pat. Nos. 2,863,752, 2,864,683 and 3,442,945 as well as in the published German application No. 2,328,340. Among these compounds, N-isopropyl-α-chloroacetanilide (propachlor), 2-methyl-6-ethyl-α-chloroacetanilide (acetochlor), 2,6-diethyl-N-methoxymethyl-α-chloroacetanilide (alachlor), 2,6-diethyl-N-butoxymethyl-α-chloroacetanilide (butachlor), 2-methyl-6-ethyl-N-(2-methoxy-1-methylethyl)-α-chloroacetanilide (metolachlor) and N,N-diallyl-α-chloroacetamide (allidochlor) gained an extended use in the agricultural practice.

However, in addition to the herbicide effect, α-chloroacetamide derivatives can also damage the cultivated plants thus, they are combined with antidotes (protecting agents), if necessary.

Antidotes compensating the phytotoxic effect on some cultivated plants of the herbicides containing thiolcarbamates as active ingredients exert a protecting action also in the case of herbicides containing α-chloroacetamide derivatives as active ingredients, particularly in the mais [J. Robert et al.: J. Agr. Food Chem. 27, 533 (1979)]. Antidotes of such type are described e.g. in the Belgian Pat. Nos. 782,120 and 806,038, in the U.S. Pat. Nos. 3,893,838 and 3,931,313 as well as in the Hungarian Pat. Nos. 165,736; 168,977; 176,784 and 183,997.

Among the antidotes, N,N-diallyldichloroacetamide reported in the Hungarian Pat. No. 165,736 gained a wide-spread use in the agricultural practice.

By using the antidotes, an enhanced selectivity contributes to the herbicidal activity of the herbicide compositions containing α-chloroacetamide derivatives.

Besides the favourable herbicidal effect and appropriate selectivity, the optimum duration of action is a further requirement against the herbicide compositions.

The concentration of the α-chloroacetamide active ingredient and that of the antidote are highest in the upper layer of the soil directly after spraying out the herbicide; however, their concentration decreases in the soil under the effect of several factors more rapidly than desired. It has been shown by the practical experience that the decomposition of α-chloroacetamide herbicides becomes more and more rapid on the repeated use in the same soil. The precocious decomposition of the herbicidally active ingredient causes the breaking-in (assault) of the weeds before the closing of the foliage of the cultivated plants and the damaging of the young cultivated plants. In the practice, this phenomenon is compensated by continuously increased doses which is, however, expensive and induces a higher polution of the environment.

This phenomenon and its reasons are reported by D. D. Kaufman and P. C. Kearney [Appl. Microbiol. 13, 443 (1965)], P. C. Kearney [J. Agr. Food Chem. 13, 369 (1965)], J. L. Fox [Science 225, 1029 (1983)] as well as by R. G. Wilson [Weed Science 32, 264 (1984)].

Based on these papers it can be stated that the active ingredients mainly those containing

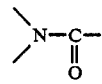

groups are decomposed by the bacteria in the soil within a few days and this ability is significantly increased when the active ingredients are repeatedly used in the same soil. This phenomenon means difficulties in the course of the practical use of α-chloroacetanilide active ingredients containing also the

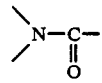

carboxylic acid amide group.

In the experiments carried out for prolonging the duration of compositions containing an α-chloroacetamide derivative and optionally an antidote it was observed that the duration of the herbicidal effect and in some cases, surprisingly the selectivity were also significantly increased when the animal derivatives of the general formula (III) (extenders) were mixed into the soil simultanously with the application of the herbicide composition. By using the extenders of the general formula (III) the optimum duration of the herbicidal effect can be regulated, the dose of the employed active ingredient can be decreased and its selectivity increased.

By using the extenders, the herbicide compositions containing an α-chloroacetamide active ingredient and optionally an antidote can be used for important cultivated plants such as for maise, sunflower, sugar-beet, vegetables, fruits and the like, more favourably than the compositions used so far which contain only an α-chloroacetamide derivative and optionally an antidote.

The compounds of the general formula (III) can be prepared by using methods known in the art.

The compounds of the general formula (III) in which $R_5$ and $R_6$ are the same as $R_7$ and $R_8$; or $R_5$, $R_6$, $R_7$ and $R_8$ are the same, can be prepared by reacting one mole of a secondary amine of the general formula

with 0.5 mole of an aldehyde of the general formula

wherein $R_{10}$ and $R_{11}$ are different from another but the same as $R_5$ and $R_6$ or as $R_7$ and $R_8$, respectively, or $R_{10}$ and $R_{11}$ are the same as $R_5$, $R_6$, $R_7$ and $R_8$ while $R_9$ is as defined above.

When at least one of $R_5$, $R_6$, $R_7$ or $R_8$ is different from the others, then the compounds of the general formula (III) are prepared by reacting 0.5 mole of a secondary amine of the general formula

and 0.5 mole of a secondary amine of the general formula

with 0.5 mole of an aldehyde of the general formula

This reaction can be carried out in water or in the presence of or without an inert solvent or diluent.

The product obtained is separated from the aqueous phase, extracted if necessary, then the solvent is evaporated. The product is dried and eventually distilled. In general, the crude product obtained after drying may directly be used.

The invention is illustrated by the following non-limiting Examples.

EXAMPLE 1

N,N'-Diallyl-N,N'-diethyldiaminomethane 85.0 g (1 mole) of ethylallylamine are placed into a round bottom flask of 250 ml fitted with a stirrer, reflux condenser, thermometer and dropping funnel. 40.5 ml (0.5 mole) of 37% formaldehyde solution are dropped in while stirring at such a rate that the temperature of the mixture remains below 60° C. Then the mixture is heated in water bath while stirring for 2 hours, then cooled down, separated from the aqueous phase and dried over anhydrous sodium sulphate. The dried crude product is obtained in a yield of 89 g (98%). On distillation the title product is obtained in a yield of 83.7 g (92%) as a colourless liquid, b.p. 78°–80° C./2 kPa, $n_D^{20} = 1.4431$.

EXAMPLE 2

N,N,N',N'-Tetra-(n-butyl)-diaminoethane 129.25 g (168.3 ml, 1 mole) of di-n-butylamine are placed into a 250-ml round bottom flask fitted with a stirrer, reflux condenser, thermometer and dropping funnel. 40.5 ml (0.5 mole) of 37% formaldehyde solution are dropped in while stirring at such a rate that the temperature of the mixture remains below 60° C. Then the mixture is heated in a water bath while stirring for 2 hours, cooled down, separated from the aqueous phase and dried over anhydrous sodium sulphate. The dried product is obtained as a light-yellow liquid in a yield of 122 g (90%), $n_D^{20} = 1.4417$.

EXAMPLE 3

N,N,N',N'-Tetraisopropyldiaminomethane 101.2 g (140.2 ml, 1 mole) of diisopropylamine are placed in a 250-ml round bottom flask fitted with a stirrer, reflux condenser, thermometer and dropping funnel. 40.5 ml (0.5 mole) of 37% formaldehyde solution are dropped in while stirring at such a rate that the temperature of the mixture remains below 40° C. Then the mixture is stirred at a temperature between 45° and 55° C. for 2 hours, cooled down, separated from the aqueous phase and dried over anhydrous sodium sulphate to give 91 g (85%) of the dried title product, $n_D^{20} = 1.4140$.

EXAMPLE 4

N,N'-Dihexyldiaminomethane 101.2 g (132.8 ml, 1 mole) of hexylamine are placed into a 250-ml round bottom flask fitted with a stirrer, reflux condenser, thermometer and dropping funnel. 40.5 ml (0.5 mole) of 37% formaldehyde solution are dropped in while stirring at such a rate that the temperature of the mixture remains below 60° C. Then the mixture is heated in a water bath while stirring for 2 hours, cooled down, separated from the aqueous phase and dried over anhydrous sodium sulphate to give 93.3 g (87%) of the dried title product, $n_D^{20} = 1.4422$.

EXAMPLE 5

N,N,N',N'-Tetraallyldiaminomethane 97.2 g (122.4 ml, 1 mole) of diallylamine are placed into a 250-ml round bottom flask fitted with a stirrer, reflux condenser, thermometer and dropping funnel. 40.5 ml (0.5 mole) of 37% aqueous formaldehyde solution are dropped in while stirring at such a rate that the temperature of the mixture remains below 50° C. Then the mixture is stirred in a water bath for 2 hours, then cooled down, separated from the aqueous phase and dried over anhydrous sodium sulphate to give a dried crude product in a yield of 101 g (97%). On distillation of the crude product 97 g (94.5%) of the title compound are obtained, b.p. 96°–98° C./2 kPa, $n_D^{24} = 1.4670$ (literature value $n_D^{25} = 1.4668$).

EXAMPLE 6

N,N'-Dicyclohexyldiaminomethane 99.17 g (121 ml, 1 mole) of cyclohexylamine are placed into a 250-ml round bottom flask fitted with a stirrer, reflux condenser thermometer and dropping funnel. 40.5 ml (0.5 mole) of 37% aqueous formaldehyde solution are dropped in while stirring at such a rate that the temperature of the mixture remains below 75° C. Then the mixture is heated at 65°-75° C. while stirring for 3 hours, then cooled down and the crystalline product precipitated is washed with water to give 88.2 g (84%) of the dried title product as a white crystalline substance, m.p. 72.5°-74° C.

EXAMPLE 7

N,N'-Diethyl-N,N'-dicyclohexyldiaminomethane 127.2 g (146 ml, 1 mole) of N-ethylcyclohexylamine are placed into a round bottom flask fitted with a stirrer, reflux condenser, thermometer and dropping funnel. 40.5 ml (0.5 mole) of 37% aqueous formaldehyde solution are added while stirring at such a rate that the temperature of the mixture remains below 60° C. Then the mixture is heated at 40°-60° C. while stirring for 2 hours, cooled down, separated from the aqueous phase and dried over anhydrous sodium sulphate to give 122.6 g (92%) of the dried title product as a light-yellow liquid, $n_D^{20} = 1.4768$.

EXAMPLE 8

N,N'-Diallyldiaminophenylmethane 57.1 g (75 ml, 1 mole) of allylamine are placed into a round bottom flask fitted with a stirrer, reflux condenser, thermometer and dropping funnel. While stirring 53.1 g (51 ml, 0.5 mole) of benzaldehyde are dropped in at such a rate that the temperature of the mixture remains below 60° C. Then the mixture is heated in a water bath while stirring for 2 hours, cooled down and 100 ml of benzene are added. The benzene is distilled off and the thus-obtained product is dried over anhydrous sodium sulphate to give 81.4 g (81%) of the title compound, $n_D^{20} = 1.5571$.

EXAMPLE 9

N,N'-Diallyl-N,N'-dicyclohexyldiaminomethane 138 g (1 mole) of N-allylcyclohexylamine are weighed into a round bottom flask fitted with a stirrer, reflux condenser, thermometer and dropping funnel. While stirring 40.5 ml (0.5 mole) of 37% aqueous formaldehyde solution are dropped in at such a rate that the temperature of the mixture remains below 60° C. Than the mixture is heated at 50°-60° C. while stirring, cooled down, separated from the aqueous phase and dried over anhydrous sodium sulphate to give the dried title product in a yield of 131 g (91%), $n_D^{24} = 1.4852$.

The structure (composition) and the physical constants (boiling point and refractive index) of aminal derivatives of the general formula (III) prepared as described in the Examples are summarized in Table I.

TABLE I

| Sign | Extender | Boiling point °C./kPa | Refractive index $n_D^{20}$ | Boiling point of the starting amine (at 101.325 kPa) °C. |
|---|---|---|---|---|
| A | N,N,N',N'—Tetraallyl-diaminomethane | 96–98/2 | $n_D^{24} = 1,4670$ | 111 |
| B | N,N'—Diethyl-N,N'—diallyldiaminomethane | 98–80/2 | 1,4431 | 82–84 |
| C | N,N'—Dipropyl-N,N'—diallyldiaminomethane | 114/2,15 | 1,4501 | 110–114 |
| D | N,N'—Diisopropyl-N,N'—diallyldiaminomethane | 105–107/2,68 | 1,4430 | 96–97 |
| E | N,N'—Diisobutyl-N,N'—diallyldiaminomethane | 122–123/2,41 | 1,4481 | 123 |
| F | N,N'—Diallyl-N,N'—di-(2-methylallyl)-diaminomethane | 124–126/2 | 1,4703 | 129 |
| G | N,N,N',N'—Tetra-(n-butyl)-diaminomethane | 152–155/2 | 1,4417 | 157–161 |
| H | N,N,N',N'—Tetraisopropyl-diaminomethane | 83–85/2,6 | 1,4140 | 80–82 |
| I | N,N'—Dihexyldiaminomethane | 123–126/2 | 1,4422 | 127–130 |
| K | N,N'—Dicyclohexyldiaminomethane | — | — | 134–135 |
| L | N,N'—Diethyl-N,N'—dicyclohexyldiaminomethane | 159–162/2 | 1,4768 | 163–166 |
| M | N,N'—Diallyldiaminophenylmethane | 48–50/3,9 | 1,5571 | 52–55 |
| N | N,N'—Diallyl-N,N'—dicyclohexyldiaminomethane | 154–167/2 | 1,4852 | 65–66/1,6 kPa |

The secondary amines required for the preparation of the aminal derivatives of the general formula (III) are known compounds and commercially available or can be prepared by using methods which are analogous to those known from the literature. Ethylallylamine can be prepared e.g. by reacting allylamine with ethyl chloride [J. Am. Chem. Soc. 65, 676 (1943)].

The aminal derivatives of the general formula (III) of the invention can be used for prolonging the action and for increasing the selectivity of herbicide compositions containing α-chloroacetamide derivatives, particularly α-chloroacetamide derivatives of the general formula (I) as active ingredients. In the general formula (I)

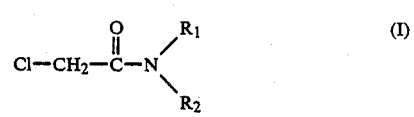

$R_1$ stands for a $C_{1-4}$ alkyl group, a $C_{2-5}$ alkenyl group or a phenyl group optionally mono- or polysubstituted by a $C_{1-4}$ alkyl group and/or halogen;

$R_2$ stands for a $C_{1-4}$ alkyl group, a $C_{2-5}$ alkenyl group, a $C_{1-4}$ alkoxyalkyl group or a pyrazolyl($C_{1-4}$ alkyl) group.

The above-mentioned alkyl groups may contain a straight or branched carbon chain and preferably are methyl, ethyl or isopropyl groups. The alkenyl group is preferably an allyl group. The phenyl group is preferably mono- or polysubstituted by a methyl, ethyl or isopropyl group and/or chlorine. The alkoxyalkyl group may contain a straight or branched carbon chain and preferably is a methoxymethyl, ethoxymethyl, butoxymethyl or 2-methoxy-1-methylethyl group.

In order to increase the selectivity, the herbicide compositions containing α-chloroacetamide derivatives as active ingredients may also contain an antidote (protecting agent). The appropriate antidotes for compositions containing α-chloroacetamide derivatives, particularly α-chloroacetamides of the general formula (I) as active ingredients, are mainly the dichloroacetamide derivatives of the general formula (II),

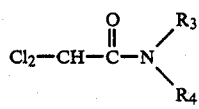

wherein $R_3$ and $R_4$ stand independently for a $C_{2-4}$ alkenyl group, a ($C_{1-4}$ alkoxy)-($C_{1-4}$ alkoxy)-($C_{1-4}$ alkyl) group or a ($C_{2-4}$ alkenyl)-aminocarbonyl-($C_{1-4}$ alkyl) group; or $R_3$ and $R_4$ together can form a saturated 4–7 membered ring optionally broken by an oxygen atom and optionally substituted by not more than 3 methyl groups or containing a $C_{5-6}$ spiro-cycloalkyl group in position 2.

The extenders of the invention can be used particularly favourably for increasing the duration of action and selectivity of herbicide compositions containing N-isopropyl-α-chloroacetanilide, 2-methyl-6-ethyl-N-ethoxymethyl-α-chloroacetanilide, 2,6-diethyl-N-methoxymethyl-α-chloroacetanilide, 2,6-diethyl-N-butoxymethyl-α-chloroacetanilide, 2-methyl-6-ethyl-N-(2-methoxy-1-methylethyl)-α-chloroacetanilide and N,N-diallyl-α-chloroacetamide as active ingredients and optionally an antidote.

The necessity and success of using the extenders is not influenced by the presence of the antidotes used for the further increase in the selectivity of the compositions containing α-chloroacetamide derivatives as active ingredients. The most favourable antidotes are N,N-diallyldichloroacetamide, N-allyl-N-ethoxyethoxymethyl-dichloroacetamide, 2,2,5-trimethyl-N-dichloroacetyloxazolidine, N,N-hexamethylenedichloroacetamide, 2,2-spiro-cyclohexyl-N-dichloroacetyloxazolidine, N-allyl-N-dichloroacetylglycine allylamide, 2-methyl-2-dichloromethyldioxolane and 1,8-naphthalenedicarboxylic acid anhydride.

The compositions containing the extenders of the invention and the α-chloroacetamide derivatives as well as antidotes may be applied together (as mixed with another) or separately, simultaneously or successively before or after sowing, before or after sprouting at an early stage to the soil or to the plants. When they are successively applied, care must be taken that the period between the application of the extender composition and that of the herbicide composition should be as short as possible.

The mass ratio of the extender to the α-chloroacetamide active ingredient of the herbicide composition may be varied between wide limits. This ratio depends on the physical and chemical properties of the extender and that of the α-chloroacetamide derivative as well as on the cultivated plants, weeds, on the properties of the soil as well as on factors which are well-known for the man skilled in the art or can easily be determined on the basis of his special knowledges.

In the compositions of the invention the ratio of the herbicidally active ingredient to the extender is in general between 25:1 and 1:1, suitably between 10:1 and 4:1, preferably it is 6:1.

The amount of the used extender is mainly adjusted to the capacity of the soil to decompose the α-chloroacetamide derivatives. The amount is 0.2 to 10 kg, suitably 0.5 to 5 kg, preferably 1 to 2 kg for one hectare.

In the compositions of the invention the ratio of the herbicidally active agent to the used antidote is not different from the usual known ratios. The total active ingredient content amounts in general from 0.1 to 95% by mass, preferably from 1 to 90% by mass.

The highly concentrated compositions as well as the ready-for-use compositions which can be prepared therefrom by dilution, are also within the scope of the invention. The invention also relates to the compositions prepared from the herbicide composition an extender composition and optionally from an antidote and mixed in a tank or in a spraying device and optionally diluted directly before use. The active ingredient content of the composition containing only the extender may be in general from 0.1 to 95% by mass, preferably from 1 to 90% by mass.

The composition of the invention may be any solid or liquid composition which is acceptable for the agricultural use, and can be prepared and used on the basis of the physical and chemical properties of the active ingredient(s). The compositions contain the active ingredient(s) together with agriculturally acceptable solid or liquid carriers and, if desired with a surface active additive.

The compositions may also contain other additives favourably influencing the development of the effect, diminishing the volatility of the active ingredients and facilitating their use. Such additives are e.g. the protective colloids, thickening agents, adhesion promoting agents adhesives, stabilizers, solid carriers with a high adsorption capacity such as starch, etc.

In addition to the above-defined amount of the active ingredient(s), the compositions of the invention in general contain 1 to 99% by mass of a solid or liquid carrier and optionally 0.1 to 25% by mass of a surface active agent.

Any of the organic or inorganic, agriculturally acceptable materials of natural or artificial origin can be used as carrier such as clay, natural or artificial silicates, silicic acid, dolomite, kaolin, diatomaceous earth, grist of plant products and the like as solid carriers; water, alcohols, esters, ketones, mineral oil fractions, aromatic, aliphatic or cyclic hydrocarbons, halogenated hydrocarbons, dimethylformamide, dimethylsulphoxide, N-methylpirrolidone and the like as liquid carriers.

The surfactant may be any emulsifying agent, a dispersing or wetting agent of either ionic and/or nonionic type. Examples of these additives are the salts of ligninsulphonic acid, phenolsulphonic acid and naphthalenesulphonic acid; the polycondensation products of ethylene oxide with fatty alcohols, fatty acids or fatty acid amides; alkyl aryl sulphonates, substituted phenols, such as alkylphenols and arylphenols as well as polyoxyethylated phenols.

Concerning the useful surfactants, known sources of the literature, for example the appropriate parts of "Surfactant Science Series", Ed. Marcel Dekker, Inc., New York, can be referred to.

In general, when the active ingredient or ingredients are insoluble in water and water is used as auxiliary material, for example for dilution, then the presence of at least one surface-active additive is necessary.

The solid compositions of the invention may be powders, dusts or granules. The liquid compositions, that is, the compositions applied in a liquid form, can be solutions, emulsifiable concentrates, emulsions, concentrated suspensions, wettable powders or sprayable powders as well as pastes. The concentrated compositions can adequately be diluted.

The compositions can be prepared in a known manner.

The compositions of the invention may also be used together with other plant protecting agents such as other herbicides, pesticides, fungicides, bactericides and plant growth regulators. In general, any plant protecting agent is useful for the combined use which is compatible with α-chloroacetamide derivatives.

The invention also relates to a process of plant protection which comprises treating the plants or the soil sown with the seeds of the plants with a herbicide composition containing an α-chloroacetamide derivative and with an extender composition of the invention simultaneously or successively, optionally in the presence of an antidote. The treatment may be carried out by using a composition containing the α-chloroacetamide derivative active ingredient and the extender as well as optionally an antidote. The active ingredients are taken in such amounts as to achieve an effective weed killing.

The compositions may be applied optionally in an appropriately diluted form by using known methods and devices such as spraying, dusting, spreading, atomization and the like.

The components and preparation of some characteristic representatives of each compositions of the invention are illustrated in the following non-limiting Examples.

COMPOSITIONS

I. Concentrate 95 parts by mass of N,N,N',N'-tetraallyldiaminomethane (extender A) are mixed with 5 parts by mass of Tween 60 emulsifier to give a concentrate containing 95% by mass of the extender. This concentrate can easily be transported, stored and applied as a stable sprayable emulsion, after dilution with water.

II. Emulsifiable concentrate 40 parts by mass of 2,6-diethyl-N-methoxymethyl-α-chloroacetanilide (alachlor) are dissolved in the mixture of 22 parts by mass of xylene and 22 parts by mass of dichloromethane. After dissolution of the substance, 8 parts by mass of the extender A and 8 parts by mass of an 1:1 mixture consisting of a calcium alkylarylsulphonate and fatty acid polyglycol ether (Emulsogen IP-400 and Emulsogen El-400) are added. The mixture is homogenized by thorough stirring and filtered. The active ingredient content of this emulsifiable concentrate is 48% by mass and the mass ratio of the herbicide ingredient to the extender is 5:1. The composition may be diluted with water as disered to give a stable emulsion.

III. Emulsifiable concentrate 72 parts by mass of 2-methyl-6-ethyl-N-(2-methoxy-1-methylethyl)-α-chloroacetanilide (metolachlor) are mixed together with 8 parts by mass of the extender B, 8 parts by mass of the emulsifier mixture used in Example II and with 12 parts by mass of kerosene. The mixture is homogenized by intensive stirring and filtered to give an emulsifiable concentrate with an active ingredient content of 80% by mass which is miscible with water in any desired ratio. The mass ratio of the herbicide ingredient to the extender is 9:1.

IV. Wettable powder 10 parts by mass of extender C are dissolved in 20 parts by mass of acetone and the obtained solution is sprayed onto 17 parts by mass of an amorphous silicic acid carrier having a great specific surface. The acetone is eliminated by drying. To the thus-treated carrier 65 parts by mass of N-isopropyl-α-chloroacetanilide (propachlor), 2 parts by mass of an aliphatic sodium sulphonate (Netzer 14), 3 parts by mass of a cresol-formaldehyde condensate (Dispergiermittel 1484) and 5 parts by mass of a powdered sulphite liquor dispersing agent are added. The mixture is homogenized, then ground to fine particles in a hammer mill (Alpine 63 C) to give a wettable powder which can be suspended in water and diluted as desired. The active ingredient content of this powder is 75% by mass, the mass ratio of the herbicide ingredient to the extender is 6.5:1.

V. Granulate 8 parts by mass of 2,6-diethyl-N-butoxymethyl-α-chloroacetanilide (butachlor), 2 parts by mass of extender E, 1 part by mass of polyethyleneglycol and 1 part by mass of a fatty alcohol polyglycol ether are dissolved in 20 parts by mass of dichloromethane. The solution is sprayed onto 88 parts by mass of a calcinated silicic earth carrier (with a particle size of 0.2 to 1.0 mm) while stirring. The solvent is evaporated to give a granulate with a total active ingredient content of 10% by mass. This granulate may be spred to the field to be treated. The mass ratio of the herbicide ingredient to the extender is 4:1.

Compositions containing other α-chloroacetamide herbicidally active ingredient and an extender can be prepared by using analogous processes to those described in Examples I to V.

The capacity of the extenders of the general formula (III) to delay the decomposition in the soil of the α-chloroacetamides of the general formula (I) was studied in laboratory experiments.

EXAMPLE A 0.6 mg of N-isopropyl-α-chloroacetanilide (propachlor) and in one series 0.05; 0.1; 0.2; 0.4 and 0.8 mg, respectively, of extender A were uniformly mixed into 100 g of air-dried loamy-sandy field soil (with a humus content of 1.7% by wt., pH=6.8) each. The treatment with propachlor was carried out in such a way that 1 g of a commercially available herbicide (Satecid 65 WP) was suspended in 1 liter of water, 0.92 ml of the suspension was taken out, made up to 5 ml, poured onto the soil sample of 100 g and mixed thoroughly. The treatment with the extender was carried out in such a manner that 0.1 g of the emulsifiable concentrate prepared from the extender A is described in Example I was emulsified in 1 liter of water, then 0.48; 0.96; 1.90; 3.80 and 7.60 ml, respectively, of the emulsion was added to the soil sample of 100 g previously treated with propachlor, finally the soil was mixed thoroughly. Thereafter the soil samples were placed in culture bottles, wetted up to 80% of their water adsorption capacity and then incubated at a temperature of $25\pm3°$ C. under a light intensity of 300 lux for 6 days. Then 150 ml of ethyl acetate each were given to the soil samples and the thus-formed soil suspensions were thoroughly mixed by using a laboratory stirrer for 10 minutes. The propachlor content of the separated solvent phase was determined by using gas-liquid chromatography after partial evaporation under reduced pressure. The results are summarized in Table II.

TABLE II

Alteration of the decomposition of N—isopropyl-α-chloroacetanilide (propachlor) under the effect of various amounts of N,N,N',N'—tetraallyldiamino-methane (extender A)

| | Weighed-in propachlor + extender A | | Obtained propachlor |
|---|---|---|---|
| | mg | mg | mg |
| 0 | 0.6 | — | 0.075 |
| 1 | 0.6 | +0.05 | 0.10 |
| 2 | 0.6 | +0.1 | 0.12 |
| 3 | 0.6 | +0.2 | 0.17 |
| 4 | 0.6 | +0.4 | 0.15 |
| 5 | 0.6 | +0.8 | 0.21 |

It can be stated that the decomposition in the soil of propachlor can significantly diminished by using the extender A.

Subsequently, it was studied in biological experiments how the duration of the action of acetochlor or alachlor as α-chloroacetamide derivatives of the general formula (I) was increased and how their phytotoxicity was influenced by the extenders of the general formula (III).

EXAMPLE B 700 g of an air-dried, loamy-sandy field soil (with a humus content of 7.1% by wt., pH=6.8) each led through a sieve with apertures of 2 mm in diameter, were placed in culture bottles.

An aqueous emulsion prepared from a commercially available composition containing 50% by wt. of acetochlor (MG-02 50 EC) or a composition containing 48% by wt. of alachlor (Lasso) was sprayed onto the soil surface in such an amount as to give an active ingredient dose of 2 kg/hectare of acetochlor or 2 kg/hectare of alachlor, respectively, by considering the dimensions of the culture bottle. Thereupon, aqueous emulsions prepared from the emulsifiable concentrates obtained from the extenders A, B, C, D, E, F, G, H, J, K, L, M or N, respectively, as described in Example I were sprayed in each bottle onto the soil surface in such an amount as to give an extender dose of 1 kg/hectare by considering the dimensions of the bottle. Then the soil was wetted up to its whole water adsorption capacity and incubated at a temperature of $25\pm3°$ C. under a light intensity of 10 lux for 14 days. Then the soil in each bottle was thoroughly mixed, halved and put into two smaller culture bottles. In one of the bottles 15 maize grains (NKPX-20) each, and in the other one 0.5 g of linseeds each were sown as weeds. The green mass of the plants were weighed 10 days after sowing. The results are summarized in Tables III and IV.

TABLE III

The development of the green mass of the flax sown as weed and treated with 2 kg/hectare of acetochlor or with 2 kg/hectare of alachlor under effect of an 1 kg/hectare dose each of the extenders A, B, C, D, E, F, G, H, J, K, L, M or N (expressed as % of the untreated control)

| Extender | Herbicide 2 kg/hectare | |
|---|---|---|
| 1 kg/hectare | Alachlor | Acetochlor |
| — | 40 | 35 |
| A | 10 | 8 |
| B | 15 | 12 |
| C | 19 | 15 |
| D | 15 | 12 |
| E | 10 | 8 |
| F | 17 | 15 |
| G | 27 | 19 |
| H | 32 | 25 |
| J | 35 | 22 |
| K | 22 | 28 |
| L | 28 | 26 |
| M | 30 | 29 |
| N | 32 | 30 |

It can be stated on the basis of Table III that the weed killing action of herbicide compositions containing alachlor or acetochlor as active ingredient is increased in the presence of the extenders of the invention.

TABLE IV

The development of the green mass of maize treated with 2 kg/hectare of acetochlor or with 2 kg/hectare of alachlor under the effect of an 1 kg/hectare dose each of the extenders A, B, C, D, E, F, G, H, J, K, L, M or N (expressed at % of the untreated control)

| Extender | Herbicide 2 kg/hectare | |
|---|---|---|
| 1 kg/hectare | Alachlor | Acetochlor |
| — | 85 | 79 |
| A | 95 | 88 |
| B | 100 | 95 |
| C | 100 | 95 |
| D | 93 | 90 |
| E | 90 | 87 |
| F | 100 | 95 |
| G | 94 | 81 |
| H | 92 | 82 |
| J | 98 | 76 |
| K | 96 | 92 |
| L | 93 | 85 |
| M | 98 | 91 |
| N | 100 | 87 |

It is obvious from the data of Table IV that the extenders of the invention also exert a protecting action in the case of the maize. The phytotoxic effect of the alachlor or acetochlor, respectively, is compensated as the decomposition of these active ingredients is delayed and their concentration becomes relatively high in the presence of the extenders.

What we claim is:

1. A herbicidal composition exhibiting prolonged effect comprising, as the herbicidally active ingredient, 2,6-diethyl-N-methoxy-methyl-α-chloroacetanilide, N-isopropyl-α-chloroacetanilide or 2-methyl-6-ethyl-N-ethoxy-methyl-α-chloroacetanilide, and an effective herbicidal effect prolonging amount of an animal derivative of the formula (III)

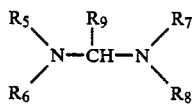

wherein
  $R_5$, $R_6$, $R_7$ and $R_8$ independently are hydrogen, $C_1$–$C_6$ alkyl, $C_3$–$C_7$ cycloalkyl, $C_2$–$C_5$ alkenyl or $C_2$–$C_5$ alkenyl substituted by $C_1$–$C_4$ alkyl; and
  $R_9$, is hydrogen, $C_1$–$C_4$ alkyl, $C_1$–$C_4$ alkyl substituted by halogen, or phenyl.

2. The composition as claimed in claim 1 containing N,N,N',N'-tetraallyldiaminomethane, N,N'-diethyl-N,N'-diallyldiaminomethane, N,N'-dipropyl-N,N'-diallyldiaminomethane, N,N'-diisopropyl-N,N'-diallyldiaminomethane, N,N'-diisobutyl-N,N'-diallyldiaminomethane, N,N'-diallyl-N,N'-di-(2-methylallyl)-diaminomethane, N,N,N',N'-tetra-(n-butyl)-diaminomethane, N,N,N',N'-tetraisopropyldiaminomethane, N,N'-dihexyldiaminomethane, N,N'-dicyclohexyldiaminomethane, N,N'-diethyl-N,N'-dicyclohexyldiaminomethane, N,N'-diallyldiaminophenylmethane or N,N'-diallyl-N,N'-dicyclohexyldiaminomethane for prolonging the effect.

3. The composition of claim 1 which also contains an effective plant protecting amount of an antidote.

4. The composition of claim 3, wherein said antidote corresponds to the formula II

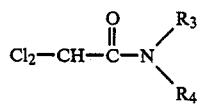

wherein
  $R_3$ and $R_4$ independently are $C_{2-4}$ alkenyl, ($C_{1-4}$ alkoxy)-($C_{1-4}$ alkoxy)-($C_{1-4}$ alkyl), or ($C_{2-4}$ alkenyl)-aminocarbonyl-($C_{1-4}$ alkyl); or $R_3$ and $R_4$ together can form a saturated 4–7 membered ring optionally containing a ring oxygen atom and optionally substituted by 1, 2 or 3 methyl groups or contain a $C_{5-6}$ spiro-cycloalkyl group in position 2.

5. The composition of claim 1, wherein said aminal derivative in N,N,N',N'-tetraallyl-diaminomethane.

6. The composition of claim 1 in combination with an agriculturally acceptable inert carrier.

7. A process for destroying undesirable plants in the presence of crop plants which comprises treating the plant or the plant environment with an effective plant destroying amount of a composition of claim 1.

8. The process of claim 7, wherein the composition also contains an effective crop plant protecting amount of an antidote.

9. A process for destroying undesirable plants in the presence of crop plants which comprises treating the plant or the plant environment in succession with 2,6-diethyl-N-methoxy-methyl-α-chloroacetanilide, N-isopropyl-methyl-α-chloroacetanilide, 2-methyl-6-ethyl-N-ethoxy-methyl-α-chloroacetanilide, and an effective herbicidal effect prolonging amount of an animal derivative of the formula (III)

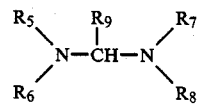

wherein
  $R_5$, $R_6$, $R_7$ and $R_8$ independently are hydrogen, $C_1$–$C_6$ alkyl, $C_3$–$C_7$ cycloalkyl, $C_2$–$C_5$ alkenyl or $C_2$–$C_5$ alkenyl substituted by $C_1$–$C_4$ alkyl; and
  $R_9$, is hydrogen, $C_1$–$C_4$ alkyl, $C_1$–$C_4$ alkyl substituted by halogen, or phenyl.

10. The process of claim 9, wherein the plant environment is also treated with an effective crop plant protecting amount of an antidote.

* * * * *